(12) United States Patent
O'Donnell

(10) Patent No.: US 8,951,787 B1
(45) Date of Patent: Feb. 10, 2015

(54) VERMICOMPOSTING APPARATUS AND SYSTEM

(76) Inventor: Lindsay Paul O'Donnell, Forest Knolls, CA (US)

( * ) Notice: Subject to any disclaimer, the term of this patent is extended or adjusted under 35 U.S.C. 154(b) by 1160 days.

(21) Appl. No.: 12/460,425

(22) Filed: Jul. 16, 2009

(51) Int. Cl.
*C05F 17/00* (2006.01)
*C12M 1/26* (2006.01)
*A01K 67/033* (2006.01)

(52) U.S. Cl.
CPC ............ *C05F 17/0009* (2013.01); *C12M 33/00* (2013.01); *A01K 67/0332* (2013.01)
USPC ...................................................... 435/290.1

(58) Field of Classification Search
CPC . C05F 17/0009; A01K 67/0332; C12M 33/00
USPC .......................... 435/290.1; 119/6.7; 206/423
See application file for complete search history.

(56) References Cited

U.S. PATENT DOCUMENTS

| | | | | |
|---|---|---|---|---|
| 3,961,603 A * | 6/1976 | Gaddie, Sr. | ..................... | 119/6.7 |
| 4,334,498 A * | 6/1982 | Bedding | ......................... | 119/6.7 |
| 4,646,682 A * | 3/1987 | Wilson | ............................ | 119/6.7 |
| D332,163 S * | 12/1992 | Appelhof | ......................... | D34/7 |
| 5,262,051 A * | 11/1993 | Iwatsuka | ........................ | 210/615 |
| 6,474,259 B1 * | 11/2002 | Gaugler | ......................... | 119/6.7 |
| 7,998,728 B2 * | 8/2011 | Rhoads et al. | ............. | 435/290.1 |
| 2007/0029247 A1 * | 2/2007 | Alpert | ........................... | 210/287 |

* cited by examiner

*Primary Examiner* — Jonathan Hurst
(74) *Attorney, Agent, or Firm* — Risto A. Rinne, Jr.

(57) ABSTRACT

An apparatus for decomposing kitchen waste by the use of vermiculture includes a container. A conduit is disposed along a bottom of the container and is attached to a spigot that exits from the container. A plurality of fluid collection openings are arranged in spaced-apart rows along a bottom of the conduit and in a cluster proximate the spigot. Gravel or other means for producing a volume for the collection of an effluent is provided along the bottom of the container up to the uppermost height of the conduit, which is sloped downward toward the spigot. A screen is placed over the conduit and gravel. A starter material is placed over the screen and provides a habitat for a preferred species of earthworm which are then added.

13 Claims, 3 Drawing Sheets

VERMICOMPOSTING APPARATUS AND SYSTEM

BACKGROUND OF THE INVENTION

1. Field of the Invention

The present invention, in general, relates to composting and, more particularly, to a composting system that creates a symbiotic environment in which worms and other microorganisms cooperate to produce a harvestable fertilizer from certain organic waste items.

A preferred type of worm is generally used in all vermicomposting devices and systems. These worms are commonly referred to as "red wigglers" or, alternately, as "red worms" and in the vermiculture art on occasion, simply as "earthworms". The preferred worm for vermicomposting is "Eistenia Fetida-Lumbricus Rebellus" and herein, when any of the above terms or "worm" or "worms" are used, reference is being made to this particular preferred species of worm. The usefulness of Eistenia Fetida-Lumbricus Rebellus in the vermiculture art is generally well known. The art of using worms for composting is referred to as "vermicomposting" or as "vermiculture".

Helping to ensure that vermicomposting worms stay alive (i.e., survive) has been a long-standing need that has not been adequately met with prior art devices and systems. This is due to many factors, one of which being that water must periodically be added to the organic material which is included with all vermicomposting devices. Subjecting the worms to prolonged immersion in the water that is added creates an environment in which the worms will drown.

Consequently, prior art devices have, of necessity, traditionally included a plurality of trays that are stacked one on top of the other and which each contain different elements or stages of the prior art systems. The trays are periodically removed and their positioning is altered. This must be done to prevent the worms from drowning or to prevent the worms from otherwise being exposed to an environment that is hostile to them.

If a user forgets to rotate the trays the worms will drown. This is because the water that is added will accumulate where the worms are located and inundate their habitat. There is no mechanism in any known prior art vermicomposting device that allows for the water to pass through the worm habitat and which will automatically channel the water to a location that is away from the worms, thereby ensuring that the worm habitat cannot flood.

Also, with all vermicomposting systems the user is instructed to only add a predetermined quantity of water to the system. Many users are unable to determine the proper quantity of water or they believe that more is better and so there is a tendency to over-water any vermicomposting system. Unlike over-watering a lawn where harm is unlikely to occur, with prior art types of vermicomposting systems over-watering is deadly to the worms because it will cause the water level to rise and enter into the worm's habitat and quickly drown the worms.

In order to optimize their chances of survival, the worms must be provided with an adequate food source, a moist pH-balanced environment conducive to the worm's mucoidal integument, an environment that is not adversely affected by a build up of their own excretions (commonly called "worm castings"), and their environment must be maintained within an acceptable range of temperature and relative humidity.

If the user of such a system fails to rotate the trays when required, worm mortality rates can skyrocket due to an environment that is becoming increasingly toxic for any of the above reasons. As mentioned earlier, this can happen quickly if a rapidly rising water level results in their drowning and it can happen more slowly if their environment should become too dry, too hot, too cold, etc.

In particular, it is desirable to maintain a relatively high amount of moisture (humidity) in a vermicomposting device. Also, other microorganisms are involved in any vermicomposting system and the worms and microorganisms work together in a symbiotic relationship to decompose the organic material so that an end-product is provided that is suitable for use as an organic fertilizer. If the worms or other essential microorganisms experience a high mortality rate the efficacy of the system (or device) can plummet or fail utterly.

It is discouraging for users to realize that their failure to accomplish a timely tray rotation (or to timely and properly accomplish some other attendant duty such as adding too much water or forgetting to add any water for several days) has caused all (or most) of the worms to die. Not only are they likely to feel great personal responsibility and remorse for these deaths, their vermicomposting device is rendered inoperative as a result of the death of the worms. The device becomes filled with decomposing worms and can emit a most foul odor.

These deficits become powerful deterrents which discourage the continued use of the prior art devices because the users feel that they are all but certain to eventually cause and again experience additional high worm mortality rates and then have to deal with the decomposing worms and additional remorse. Accordingly, there is a significant and long-standing need to provide a vermicomposting system that lessens the likelihood of a high worm mortality rate occurring.

To restore the vermicomposting system to operation the worms must be replaced, the environment adjusted to include a proper amount of moisture, the accumulated toxins and decomposing worms removed, and then given a sufficient amount of time for the environment to return to a state of equilibrium before optimum fertilizer productivity can, once again, resume. Accordingly, the user is deprived of organic fertilizer when needed.

Therefore, a significant deficit of all known prior art types of vermicomposting devices is that they all experience, from time to time, high worm and/or microorganism mortality rates. The user is generally unaware of the death of microorganisms as a result of his actions and does not typically experience remorse. The prior art devices also require periodic rotation of trays to maintain a proper environment and are at great risk of over-watering or of neglect. As such, they cannot be left unattended for more than a couple of days or worm mortality will occur. As such, they are relatively high-maintenance devices and this aspect of their use also deters many potential users. Because people commonly go on trips and vacations for longer periods of time than the prior art devices can tolerate, it is highly probable that eventually many users will fail to perform the necessary actions and as a result experience high worm mortality rates and the resultant problems, as described hereinbefore.

Furthermore, all known prior art vermicomposting devices are only intended for use and storage outside of a residence or living area that is inhabited by humans. This is because all prior art devices will, from time to time, emit noxious or unpleasant odors that generally preclude any interior usage, as was mentioned before when worms die and decompose. This, in turn, subjects all of the known prior art devices to the full range of environmental swings that occur in nature. Eventually, prolonged swings in weather, such as in the temperature or humidity are likely to be overlooked or otherwise uncompensated for by the user. This can also cause the worms of prior art vermicomposting systems to experience a high mortality rate.

The most common organic material that is added to a vermicomposting system includes any of the many varieties of kitchen vegetable waste (i.e., raw vegetables, etc.), pulverized eggshells, herbal tea remnants, and other organic waste materials that do not adversely affect the vermicomposting environment, such as the pH level. These are routinely added and provide the organic matter at the top of the food chain that is eventually broken down by the microorganisms and the worms to yield the desired fertilizer, which is contained in the worm castings.

All types of vermicomposting devices are similar in that organic matter which it is desirable to decompose is periodically added to the device and an end-product of organic fertilizer is produced and periodically removed. Water is periodically added to the device in a prescribed manner and the device is timely attended to, as instructed. The efficacy and desirability of such organic fertilizers is well known and is therefore not elaborated upon herein.

The fertilizer produced by vermicomposting devices and systems may be used to create either a dry or a wet fertilizer. As previously mentioned, the worms produce an excretion that is commonly referred to as "worm castings". The worm castings can be harvested and dried for later use as a fertilizer. The use of dry worm castings is less effective if directly applied as a fertilizer, so the worm castings are typically dissolved in water and the resultant soluble mix is then applied as a fertilizer.

Alternately, the worm castings can be harvested wet by the addition of a sufficient quantity of water to dissolve the worm castings in the water. The soluble mix is obtained and can be applied directly to growing vegetation or it may be diluted by adding additional water. Either way, the user of a prior art type of device must use their hands or some type of a tool to access the worm castings for harvest. As such, it is a generally messy procedure that few people enjoy doing. The difficulty and mess of harvesting fertilizer from prior art devices serves as a further deterrent to their use.

Also, it is highly desirable that pests such as flies be kept out of the vermicomposting system. It is common for flies to obtain access to prior art systems and devices. The presence of flies creates an environment that may introduce disease or contaminants to the system. Also, the user generally feels as if a fly-infested prior art type of device is somehow unhealthy or unsafe to use. Additionally, the attraction to flies and their presence in prior art devices further precludes their placement inside of a residence.

With all prior art systems, the user is not supplied at the time of purchase with all of the materials needed to operate the system. The user must obtain worms from an alternate source at additional expense beyond that of the systems purchase. This is a further deterrent to the use of prior art systems. Additionally, prior art systems supply only newspapers at the time of purchase as bedding material for the worms. The newspapers lack nutrients and are not conducive for promoting worm growth. Accordingly, worm mortality can occur as a result.

Accordingly, there exists today a need for a vermicomposting apparatus and system that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As various embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty. Therefore, by helping to provide a more elegant solution to various needs, some of which may be long-standing in nature, the instant invention further attests that the elements thereof, in combination as claimed, cannot be obvious in light of the teachings of the prior art.

Clearly, such an apparatus, system, and method would be useful and especially desirable.

2. Description of Prior Art

Vermicomposting devices are, in general, known. For example, the following products and/or patents describe various types of these devices, some of which may have relevance as well as others which may not have particular relevance to the invention. These patents are cited not as an admission of their having any particular relevance to the invention but rather to present a broad and diversified understanding regarding the current state of the art appertaining to either the field of the invention or possibly to other related or distal fields of invention.

U.S. Pat. No. 6,223,687 to Windle, that issued on May 1, 2001;

U.S. Patent Publication No. 2002/0144658 to Holcombe, that published on Oct. 10, 2002;

U.S. Patent Publication No. 2003/0059931 to Gitt, that published on Mar. 27, 2003;

and including the following products found on the web:

Can-O-Worms Household Composting System made by Reln;

Tumbleweed Worm Farm Compost Bin made by Tumbleweed;

Tumbleweed Pet Poo Converter made by Tumbleweed;

The Worm Factory Composting System made by The Worm Company; and

The Worm Wigwam made by Sustainable Agricultural Technologies, Inc.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a vermicomposting apparatus and system that is inexpensive to manufacture.

It is also an important object of the invention to provide a vermicomposting apparatus and system that uses red wigglers (Eistenia Fetida-Lumbricus Rebellus) as worms to help produce a fertilizer for use.

Another object of the invention is to provide a vermicomposting apparatus and system that decomposes organic vegetable matter and produces organic fertilizer in liquid form.

Still another object of the invention is to provide a vermicomposting apparatus and system that composts selected types of organic matter to produce a high potency fertilizer that is soluble in water.

Still yet another object of the invention is to provide a vermicomposting apparatus and system that composts select types of organic matter and produces a fertilizer that can be accessed by hand.

Yet another important object of the invention is to provide a vermicomposting apparatus and system that allows for the periodic addition of water to produce a quantity of liquid fertilizer for dispensing and subsequent use.

Still yet another important object of the invention is to provide a vermicomposting apparatus and system that allows for the periodic addition of water to produce a quantity of liquid fertilizer that prevents worms from drowning.

A first continuing object of the invention is to provide a vermicomposting apparatus and system that composts select types of organic matter to produce a fertilizer soluble in a liquid and which is readily dispensable from a tap.

A second continuing object of the invention is to provide a vermicomposting apparatus and system that does not require the periodic rotation of trays.

A third continuing object of the invention is to provide a vermicomposting apparatus and system that does not include removable trays.

A fourth continuing object of the invention is to provide a vermicomposting apparatus and system that decreases worm mortality.

A fifth continuing object of the invention is to provide a vermicomposting apparatus and system that provides a greater span of time of inattention and inactivity than that of prior art designs before a significant increase in worm mortality occurs.

A sixth continuing object of the invention is to provide a vermicomposting apparatus and system that includes a liquid accumulation area that is separated apart from and disposed below an area in which worms and other micro-organisms operate on the decomposition of organic matter.

A seventh continuing object of the invention is to provide a vermicomposting apparatus and system that is self-contained.

An eighth continuing object of the invention is to provide a vermicomposting apparatus and system that is available in any desired size or capacity.

A ninth continuing object of the invention is to provide a vermicomposting apparatus and system that is reliable.

A tenth continuing object of the invention is to provide a vermicomposting apparatus and system that can be sold as a complete unit including all of the ingredients necessary to begin composting as part of the sale price and wherein all of the components, including live worms, are available at the time of pickup or, alternately, wherein the live worms are prepaid at the time of purchase and which are shipped directly to the purchaser.

An eleventh continuing object of the invention is to provide a vermicomposting apparatus and system that includes a liquid collection area which includes a predetermined volume of space that is provided proximate a bottom of the apparatus and which is used for accumulating a predetermined quantity of water that contains an organic fertilizer in solution, wherein the quantity of water is periodically added at a top of the apparatus through an opening that is provided, and wherein the water percolates down through a layer of organic matter and through various stages of decomposing organic matter, past a quantity of worms that are disposed in a certain lower stage or stages of the decomposing organic matter and which are aiding in the decomposition of the organic matter, continuing downward through a screen, and arriving in the liquid collection area as a fertilizer in soluble form.

A twelfth continuing object of the invention is to provide a vermicomposting apparatus and system that includes an internal collection pipe with vent holes disposed through an upper area and fertilizer collection openings disposed along a bottom thereof.

A thirteenth continuing object of the invention is to provide a vermicomposting apparatus and system that includes an internal collection pipe in a container which is pitched toward a valve that is disposed at an exterior of the container and with a clustering of fertilizer collection openings disposed at an end of the collection pipe that is nearest the valve in an interior of the container and disposed proximate a bottom thereof.

A fourteenth continuing object of the invention is to provide a vermicomposting apparatus and system that includes a screen in a container that retains worms and matter for composting above the screen and which allows water to drain down through an interior of the container and accumulate in a liquid collection area that is disposed below the screen.

A fifteenth continuing object of the invention is to provide a vermicomposting apparatus and system that includes a sheet of material that can optionally be placed on top of a screen and wherein the sheet of material can be used for hand-collection of a fertilizer.

A sixteenth continuing object of the invention is to provide a vermicomposting apparatus and system that includes an internal collection pipe in a container with fertilizer collection openings disposed along an underside of the collection pipe and on opposite sides of a bottom centerline, thereby creating a center longitudinal path for liquid that has accumulated in the collection pipe to flow downward and toward an exterior drain location.

A seventeenth continuing object of the invention is to provide a vermicomposting apparatus and system that can be used by an individual or family or small group of people to produce a proportionate amount of fertilizer.

An eighteenth continuing object of the invention is to provide a vermicomposting apparatus and system that can be used by a large group of people to produce a proportionate amount of fertilizer.

A nineteenth continuing object of the invention is to provide a vermicomposting apparatus and system that can be placed in areas where the public is likely to visit and wherein the system can be used by a large number of people to produce a proportionate amount of fertilizer, and wherein each user would be asked to contribute some approved organic waste material into an upper portion of a container and by doing so the user would be entitled to remove a predetermined quantity of organic fertilizer therefrom in return.

A twentieth continuing object of the invention is to provide a vermicomposting apparatus and system that includes a container and a lid and is portable.

A twenty-first continuing object of the invention is to provide a vermicomposting apparatus and system that lessens the amount or frequency of actions by a user necessary to retain a favorable environment for worms and desirable microorganisms inside of the apparatus and system.

A twenty-second continuing object of the invention is to provide a vermicomposting apparatus and system that does not clog, and is therefore reliable.

A twenty-third continuing object of the invention is to provide a vermicomposting apparatus and system that includes vents and wherein the vents permit air to flow into a container and wherein the vents include screens that prevent flies from entering therein.

A twenty-fourth continuing object of the invention is to provide a vermicomposting apparatus and system that keeps flies and other undesirable life forms from entering into an interior of a container that is provided.

A twenty-fifth continuing object of the invention is to provide a vermicomposting apparatus and system that provides a fail-safe means to prevent worms from drowning when water is added to the apparatus.

A twenty-sixth continuing object of the invention is to provide a vermicomposting apparatus and system that provides a fail-safe means to prevent worms from drowning if an excessive quantity of water is added to the apparatus.

A twenty-seventh continuing object of the invention is to provide a vermicomposting apparatus and system that can be used indoors.

A twenty-eighth continuing object of the invention is to provide a vermicomposting apparatus and system that maintains proper humidity.

A twenty-ninth continuing object of the invention is to provide a vermicomposting apparatus and system that increases the amount of time a vermicomposting system can be left unattended.

A thirtieth continuing object of the invention is to provide a vermicomposting apparatus and system in which all components necessary to operate the system are included in the purchase price.

A thirty-first continuing object of the invention is to provide a vermicomposting apparatus and system that includes a nutrient-rich food conducive to the worms at the time of purchase.

Briefly, a vermicomposting apparatus and system that is constructed in accordance with the principles of the present invention has a container that preferably includes a lid. A conduit is disposed along a bottom of the container and is closed at a first end that is disposed in the container. A second end of the conduit is attached to a spigot that exits from the container proximate an opposite second end of the conduit. Gravel or other means for producing a volume for liquid collection that includes a predetermined minimum volume is provided along a bottom of the container. The gravel or other means for producing a volume is also used to pitch the conduit wherein the first end of the conduit is disposed at a higher elevation than the second end when the container is disposed on a level surface. The conduit includes vent holes along an upper surface thereof and fluid collection openings along a lower portion thereof. A screen is disposed over the conduit and gravel or over the conduit and the other means for producing a volume. The screen provides a barrier that retains worms and organic materials a predetermined distance above the bottom of the container. A quantity of starter material for the worms is added that preferably supplies the worms with nutrients and a favorable starting environment. The worms are added to the starter material and blended therein. Vegetable waste and other food for decomposing is added on top of the starter material along with an initial quantity of water to moisten the starter material and the worms. At predetermined intervals a predetermined quantity of water is added from the top of the container after removing a lid. The lid is replaced and the water percolates through the organic materials and drains past the worms, gathering nutrients along the way from worm castings sufficient to make a high-potency liquid fertilizer that accumulates at the bottom in a fluid collection area that is provided by the spaces between the gravel or in the spaces provided by the other means for producing a volume. The liquid fertilizer passes through the fluid collection openings and into the conduit where it passes through the container and bears upon the spigot. The spigot is opened to extract a predetermined quantity of the liquid fertilizer. The spigot can be left open when adding water which provides a fail-safe way of preventing an interior water level from rising into the worm habitat thereby preventing any possibility of worm drowning. Because the liquid fertilizer quickly drains past the worms and collects in the fluid collection area, the worms are not subject to the risk of drowning by immersion in a rising fluid level in the container. An optional sheet of material is placed on top of the screen if hand removal of the fertilizer is desired. If hand removal of the worm castings is desired, the worms and decomposing organic material in the container above the sheet are urged to one side of the container and the fertilizer that accumulates on top of the sheet is urged off of the sheet for collection and use after allowing sufficient time for any residual worms to migrate to the side of the container containing the organic material. This process is then repeated to harvest the opposite side. The organic material is then returned to its position across the top of the entire screen.

DETAILED DESCRIPTION OF THE INVENTION

Figure 1:
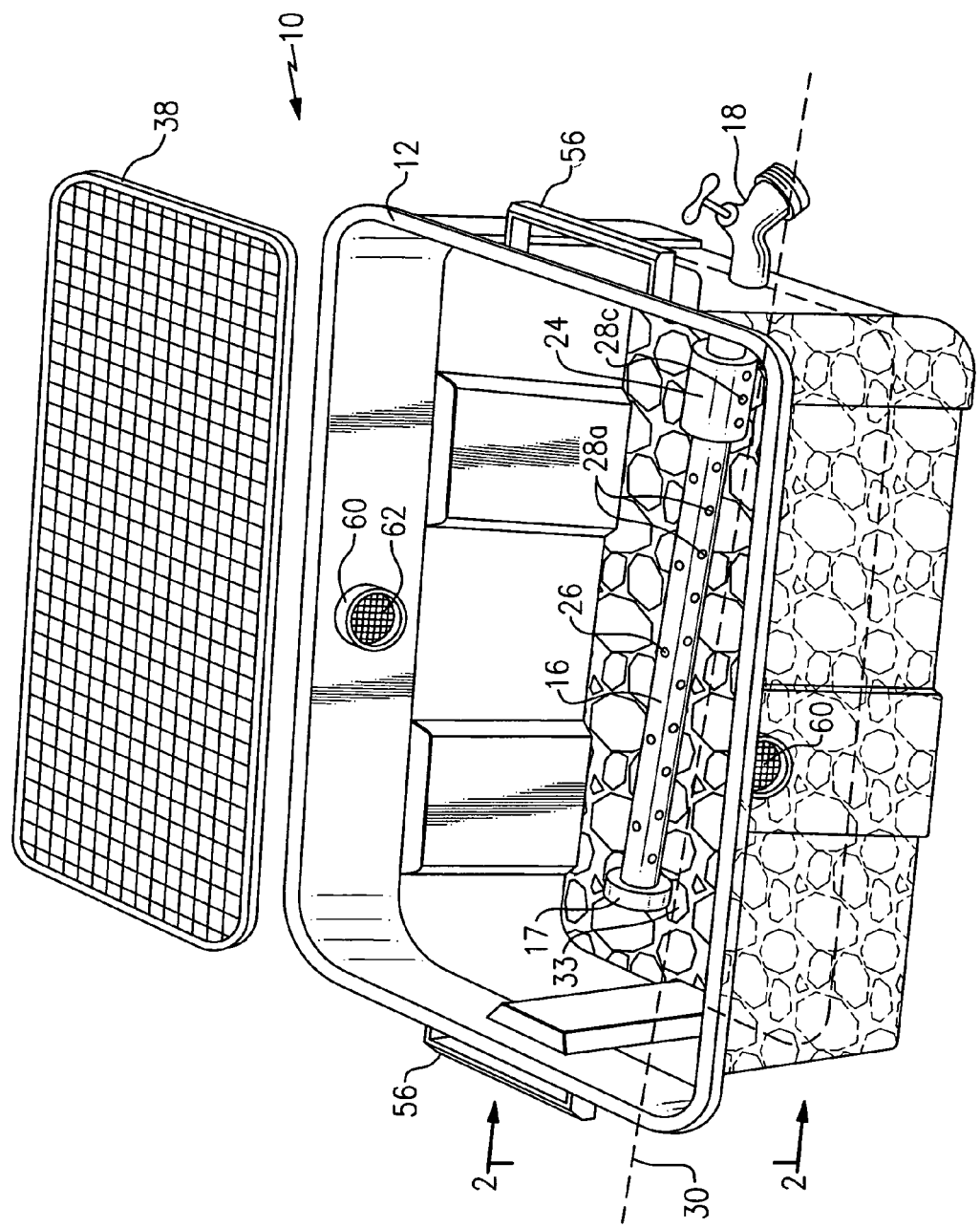
FIG. 1 is a view in perspective of a vermicomposting apparatus and system that shows the structural components with a screen disposed above the apparatus for ease of viewing of the remaining components, and which omits from view a lid and the worms and organic matter that is disposed therein during use.
Figure 2:
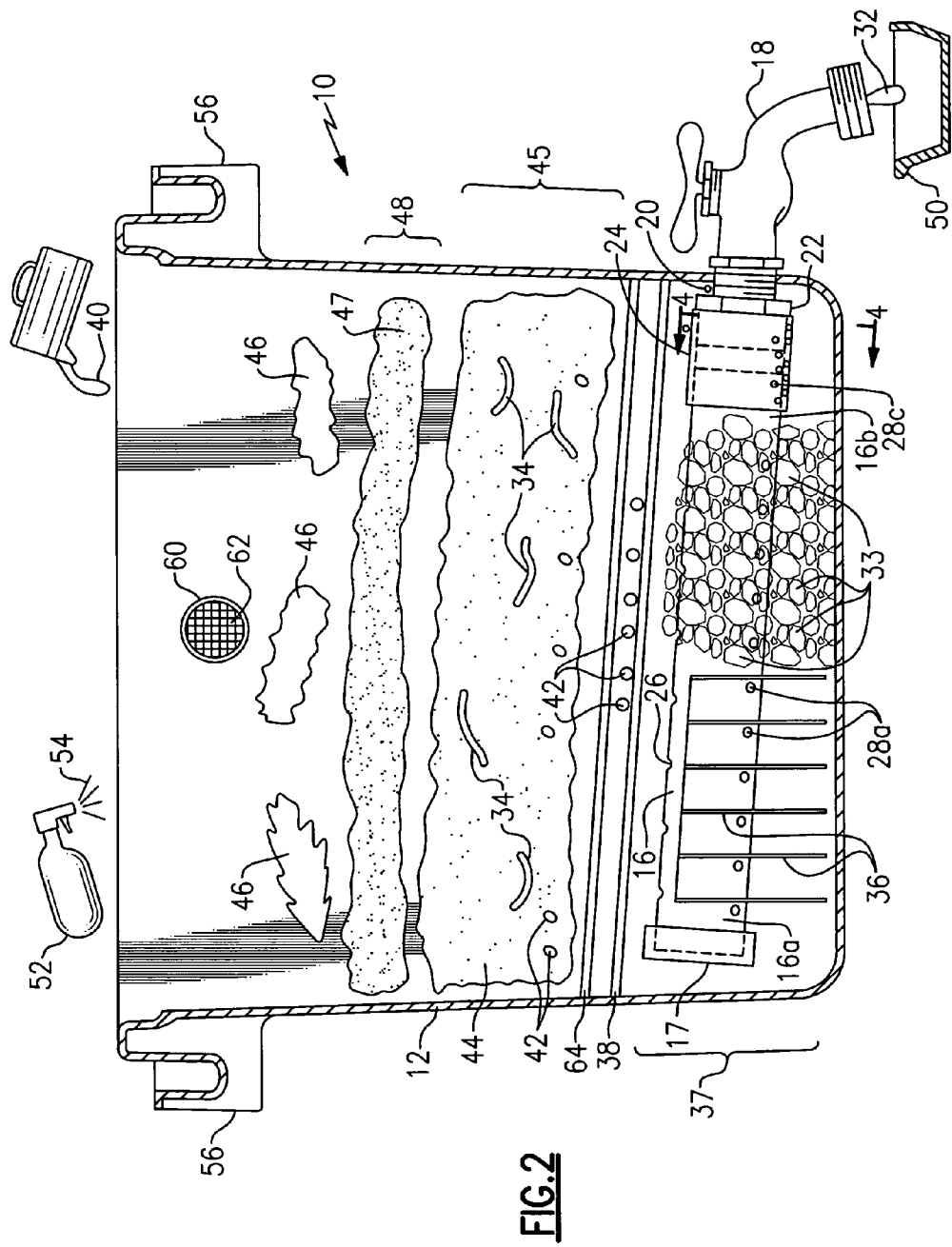
FIG. 2 is a cross sectional view taken on the line 2-2 in FIG. 1 that is taken just prior to a conduit of the apparatus and wherein FIG. 2 includes the worms and organic matter that is absent from the FIG. 1 drawing.

Referring on occasion to all of the FIGURE drawings and now, in particular to FIG. 1 and FIG. 2, is shown a vermicomposting apparatus and system, identified in general, by the reference numeral 10, and which is referred to hereinafter as "the vermicomposting device 10".

The reader will notice that reference is occasionally made throughout the DETAILED DESCRIPTION OF THE INVENTION suggesting that the reader view a particular drawing FIGURE. The suggestion is at times made when the introduction of a new element requires the reader to refer to a different drawing FIGURE and also when the timely viewing of another drawing FIGURE is believed to significantly improve ease of reading or enhance understanding. To promote optimum understanding of the instant invention the reader is encouraged to periodically refer to each enclosed FIGURE.

Figure 3:
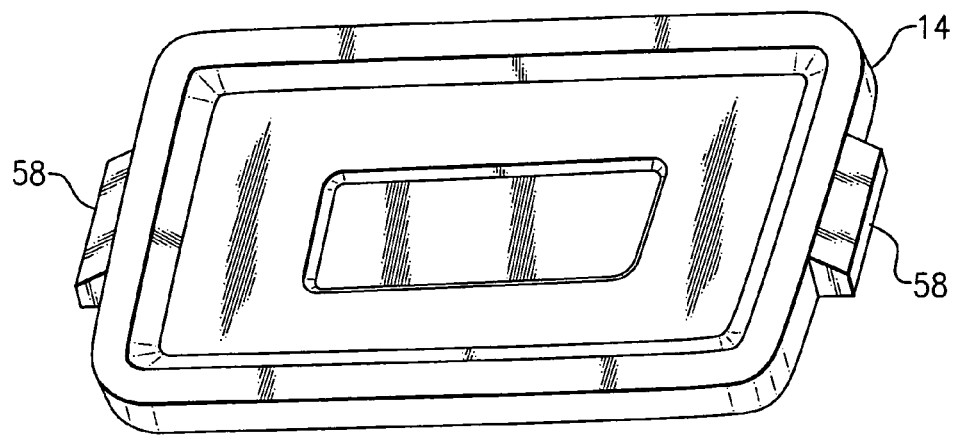
FIG. 3 is a view in perspective of a lid for the vermicomposting apparatus and system of FIG. 2.

The vermicomposting device 10 includes a container 12 with an open top that houses all aspects of the invention. A lid 14 (FIG. 3) snaps over the top of the container 12 and is removable, as needed. The container 12 is made of any preferred material and is available from any desired size from several inches in width, length, and height to many feet. If desired, the container 12 can be as large as a dumpster (not shown) or even larger for public or commercial applications. A preferred material for the container 12 includes plastic and currently available over the counter devices that are for sale can be modified for use as the container 12. A preferred size for the container 12 is about two feet long, about one and one-half feet wide, and about one and three-quarters feet tall, although these dimensions can be varied considerably.

Figure 4:
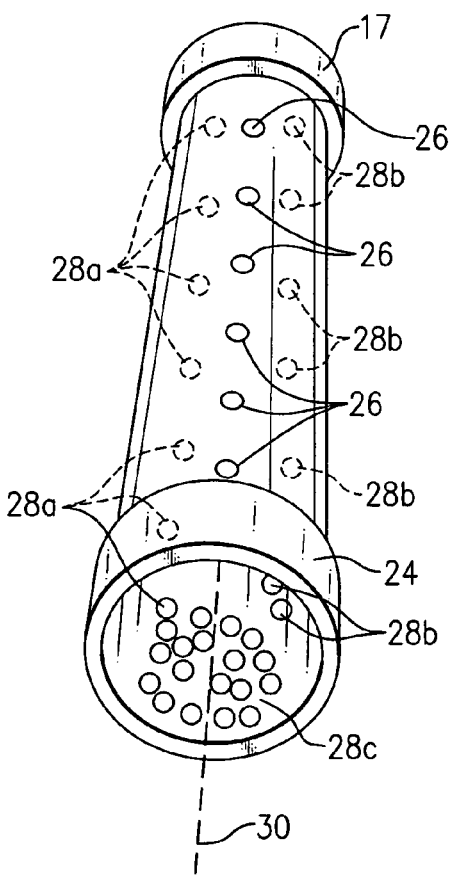
FIG. 4 is a view in perspective taken along the line 4-4 in FIG. 2 that shows a conduit of the vermicomposting apparatus and system.

A section of conduit 16 (see also FIG. 4) is disposed along a bottom of the container 12. The conduit 16 is made of any preferred material although polyvinylchloride (PVC) is preferred. A PVC end cap 17 is secured over a first end 16a of the conduit 16. A second end 16b of the conduit 16 is attached to a spigot 18 that exits from the container 12 through a container bottom hole that is provided in the container 12 for this purpose.

A preferred spigot 18 is a ¾ inch hose bib (i.e., a valve or faucet) that includes ¾ inch pipe threads that are covered with Teflon tape and which is screwed into the container bottom hole. The size of the container bottom hole is equal to a smaller size of the pipe threads which continually increase in diameter as the spigot 18 is screwed into the container bottom hole, thereby helping to provide a seal.

An O-ring 20 is included on an inside of the container 12 over that portion of the spigot's 18 ¾ inch pipe threads that extend into an interior of the container 12. The O-ring 20 abuts an adapter fitting 22 that includes ¾ inch pipe threads on an end thereof that is proximate the spigot 18. After the spigot 18 is installed the adapter fitting 22 is tightened over the spigot's 18 inward-protruding pipe threads sufficient to cause the O-ring 20 to bear tightly against the inside of the container 12 thereby ensuring a seal that prevents any fluid from leaking out of the container 12 through the container's bottom hole.

A first half of a coupling 24 is secured over the adapter fitting 22 and the second end 16b of the conduit 16 is urged into the remaining half of the coupling 24 and secured thereto.

The conduit 16 includes vent holes 26 that are disposed along an upper surface thereof along the longitudinal length of the conduit 16. The conduit 16 includes two rows of fluid collection openings 28a, 28b that extend proximate a bottom center longitudinal line of the conduit 16, as shown by dashed line 30. Each of two rows of the fluid collection openings 28a, 28b are preferably separated on opposite sides of the bottom center longitudinal line 30 by approximately 30 degrees or arc displacement from the bottom center longitudinal line 30.

This creates a smooth interior inside the conduit 16 of approximately 60 degrees arc rotation (i.e., approximately 30 degrees on either side of the bottom center longitudinal line 30) that extends longitudinally along the bottom of the conduit 16 through which an effluent 32 (See FIG. 2) is able to flow unobstructed from proximate the end cap 17 to the coupling 24. The effluent 32 is described in greater detail, hereinafter.

The conduit 16 is pitched toward the spigot 18 so that the first end 16a of the conduit 16 is higher than the second end 16b of the conduit 16 when the container 12 is on a level surface.

A quantity of gravel 33 is placed throughout the bottom of the container 12 and is used to supply the desired pitch to the conduit 16 by placing a greater amount of the gravel 33 under the conduit 16 proximate the first end 16a than under the conduit 16 proximate the second end 16b. The gravel 33 also includes air spaces that provide a volume for liquid collection. The volume is used to collect a fluid (i.e., the effluent 32) which prevents a quantity of worms 34 from drowning. By use of a sufficient, predetermined amount of the gravel 33 a predetermined volume for liquid collection between the gravel 33 is provided. A very light type of the gravel 33 is preferred to keep the weight of the vermicomposting device 10 to a minimum. Examples of a light type of the gravel 33 include lava rock and perlite.

When the gravel 33 is used (there are other ways to provide the necessary volume for liquid collection, as described hereinafter), the gravel 33 occupies a volume that extends across the bottom of the container 12 and up around the conduit 16 to about the top of the highest point of the conduit 16. This ensures that the spaces between the gravel 33 will be able to hold the desired liquid volume. The volume for liquid collection is important and provides many unexpected benefits for the instant invention, as described in greater detail hereinafter.

An alternate method of providing the volume for liquid collection is also shown in FIG. 2, and it includes a honeycomb structure 36, similar to that found in plastic crates or even ice-cube trays (not shown). The honeycomb structure 36, when used, also extends along the bottom of the container 12 and up along the sides of the conduit 16. The honeycomb structure 36 also includes a center longitudinal radius portion that is removed for placement of the conduit 16 therein. The center longitudinal radius portion of the honeycomb structure 36 secures the conduit 16 where desired and it also provides the desired pitch.

In FIG. 2 the gravel 33 is shown only on one side, however, the gravel 33 when used would extend across the entire bottom of the container 12, as previously mentioned. Similarly, when the honeycomb structure 36 is used it, too, will extend across the entire bottom of the container 12.

The volume occupied by the conduit 16 and the gravel 33 is defined by a first zone, as shown by bracket 37. The first zone 37 includes the necessary space (volume) for fluid collection and the means for accumulating the effluent 32 in the conduit 16 and directing it out of the container 12 and through the spigot 18, as desired.

A screen 38 is placed over the conduit 16 and the gravel 33 or, alternately, over the conduit 16 and the honeycomb structure 36. The screen 38 is similar to a type of screening as is used on a window or screened type of door and is used to provide a barrier that retains the worms 34 and larger organic matter above the screen 38 and allows water 40 that is periodically added to a top of the container 12 (after removing the lid 14) to dissolve a quantity of accumulated worm castings 42 and, together with the dissolved worm castings 42, to pass through the screen 38 and accumulate in the first zone 37.

The screen 38 is at least as large as the interior length and width of the container 12 to ensure that the barrier that is provided is effective.

A quantity of starter material 44 is included with the vermicomposting device 10 and the starter material 44 is placed on top of the screen 38 and the worms 34 are placed in the starter material 44. A preferred starter material 44 is a product that is offered for sale by Grab and Grow of Santa Rosa, Calif. The preferred starter material 44 is called "Mango Mulch" and is certified organic and includes apple and grape pumice which provides an effective bedding for the worms 34. This ensures that the worms 34 will have an optimum chance for survival when added to the vermicomposting device 10. Of course, other suitable material can be used as the starter material 44. It is also noted that, if desired, manure can be used and added to the starter material 44 when it is desired that the vermicomposting device 10 be able to provide the effluent 32 immediately upon delivery.

It is noted that whenever possible the starter material 44 and the worms 34 are added on top of the screen 38 at the time of sale, thereby providing the customer with a fully functioning and working vernicomposting device 10. If the worms 34 are, for any reason, not available at the point of purchase, it is preferred to include a certificate at the time of purchase that entitles the customer to receive a quantity of worms 34 from the nearest supplier of the worms 34 via mail. The customer, in that, case, mails the certificate to the nearest supplier who mails the worms 34 to the customer. Typically, the worms 34 will arrive in a few days after mailing the certificate to the supplier so the customer is assured of a functioning vermicomposting device 10 either immediately (if the worms 34 are supplied at the time of purchase) or shortly thereafter. In either situation the customer does not have to locate or travel to a supplier of the worms 34. This provides, in essence, one-stop shopping where the customer is supplied with everything that is needed at the time of purchase.

The starter material 44 becomes thick with an abundance of the worms 34 and its volume can increase as additional decomposition occurs in the vermicomposting device 10. The volume occupied by the starter material 44, the worms 34, and the additional organic matter that has been decomposed form a second zone, as shown by bracket 45. The second zone 45 defines the area inhabited by the worms 34 and it extends upward from the screen 38 for a predetermined, but somewhat variable height.

Kitchen vegetable waste 46 and other kitchen waste suitable for use is periodically added on top of the starter material 44 along with an initial quantity of the water 40 to moisten the starter material 44 (if needed) and the worms 34. Microorganisms (not shown) begin to decompose the waste 46 and provide a partially decomposed layer 47. The volume occupied by the partially decomposed layer 47 form a third zone, as shown by bracket 48.

Although the third zone 48 and the second zone 45 are shown as distinct layers, in actuality they merge into each other and do not include a distinct delineation therebetween. What is useful to understand is the waste 46 progressively decomposes until it reaches a sufficiently decomposed state where it (or the by-products of the waste 46 as produced by the microorganisms) can be ingested as a food source by the worms 34 which then produce the desired worm castings 42. The worm castings 42 appear throughout the starter material 44 and some of them may also gravitate downward proximate the screen 38.

At predetermined intervals a predetermined quantity of the water 40 is added from the open top of the container 12 after removing the lid 14. The lid 14 is replaced and the water 40 percolates through the organic waste 46 materials, through the partially decomposed layer 47, through the starter material 44, through the screen 38 and it accumulates in the first zone 37 between the gravel 33 or in the spaces of the honeycomb structure 36.

As the water 40 drains downward it dissolves the worm castings 42 into solution and carries them through the screen 38 in water-soluble form. As the water 40 picks up the dissolved castings 42 it becomes the effluent 32 which is now nutrient-rich and suitable for use as a liquid fertilizer that can be applied to growing plants. In this manner, the user is able to control the waste 46 that is used and thereby obtain a high quality fertilizer which is the effluent 32, use the effluent 32 as a fertilizer (all preferably organic), grow more food, and produce more waste 46 to continue using the vermicomposting device 10 in a balanced cyclical manner.

The volume for fluid collection provided by the gravel 33 (or the honeycomb structure 36) ensures that the fluid level of the effluent 32 in the bottom of the container 12 does not rise up higher than the screen 38. This prevents drowning of the worms 34 and greatly decreases the worm 34 mortality rates. The effluent 32 provides a liquid form of the fertilizer that is convenient to use. The effluent 32 is collected in a suitable vessel 50 and applied directly to growing vegetation as a fertilizer or it is thinned by adding a quantity of the water 40 to the effluent 32 in the vessel 50.

Some of the effluent 32 may drip on the conduit 16 and enter the interior of the conduit 16 by passing through the vent holes 26. This is fine. As the effluent 32 level rises it passes through the fluid collection openings 28a, 28b and enters into the conduit 16. It accumulates in the conduit 16 and bears upon and enters into the spigot 18. The spigot 18 is opened to extract a predetermined quantity of the liquid fertilizer effluent 32.

A cluster of fluid collection openings 28c (See FIG. 4) are provided through the bottom of the coupling 24. The cluster of fluid collection openings 28c is important in that they permit the lowest level of the effluent 32 to enter into the conduit 16 and reach the spigot 18, thereby increasing the amount of effluent 32 that can be obtained. This also is that portion of the effluent 32 that is the richest with worm castings 42 and therefore the most beneficial. Accordingly, the cluster of fluid collection openings 28c produces a stronger and better liquid fertilizer than can be obtained in their absence.

The spigot 18 is preferably left open when adding the water 40 which provides a fail-safe way of preventing the effluent 32 level from rising above the screen 38 and entering into the worm 34 habitat thereby preventing any possibility of worm 34 drowning. Even if the user inadvertently adds an excessive quantity of the water 40 to the vermicomposting device 10 there is no danger of the worms 34 drowning if the spigot 18 is left open.

Because the liquid fertilizer quickly drains past the worms 34 and collects in the fluid collection area (i.e., the first zone 37), the worms 34 are not subjected to the risk of drowning by immersion in a rising effluent 32 level within the container 12.

A spray mister 52 is preferably included with the vermicomposting device 10 and is used to periodically spray a quantity of water in mist form 54 into the container 12 to maintain a desired humidity level therein.

Side handles 56 are provided on opposite ends of the container 12 and are used for transport of the vermicomposting device 10. A pair of matching lid handles 58 are included with the lid 14.

A pair of louvered vents 60 are included on opposite sides of the container 12, near an upper end thereof, and each vent 60 passes through a vent opening that is provided through the container 12. The vents 60 each include a circular screen 62 insert that is added to the inside of the container 12 inside the vents 60 and which is used to keep flies from entering into the container 12.

The vermicomposting device 10 provides a stable vermiculture system that can be placed inside a residence. This is because it does not accumulate or emit flies and because the low worm 34 mortality prevents offensive odors from arising in the container 12. The temperate environment that exists inside the residence extends the time that the vermicomposting device 10 can go unattended to up to a week or possibly even more.

The vermicomposting device 10 provides a liquid fertilizer on demand by adding a quantity of the water 40 when desired. While the liquid form of the fertilizer (effluent 32) is generally preferred, it is also possible to harvest the castings 42 in a dry form by hand removal. If hand removal of the castings 42 is desired an optional sheet of non-porous material 64 is placed on top of the screen 38. The non-porous material 64 can be flexible or somewhat rigid.

If hand removal of the worm castings 42 is desired, the starter material 44, the worms 34 that are disposed therein, the partially decomposed layer 47, and the waste 46 that is in the container 12 and disposed above the sheet of non-porous material 64 are urged to one side of the container 12 and the castings 42 that have accumulated on top of the non-porous material 64 are then urged by hand (or by a preferred tool) off of the non-porous material 64 and are gathered for later use after first allowing a sufficient amount of time for those few possible worms 34 that are also on the non-porous material 64 to migrate to the side of the container 12 where the starter material 44 has been urged.

This process is then repeated to harvest the castings 42 from the opposite side of the container 12. The starter material 44, the worms 34 that are disposed therein, the partially decomposed layer 47, and the waste 46 is then returned to its previous uniform position across the top of the entire screen.

If desired, the container 12 can be provided in any desired size. It is envisioned that very large units could be placed in public areas and that users could deposit their kitchen waste 46 items into the large unit and that doing so would entitle them to obtain a quantity of the effluent 32 for their own use. In this way a community-based solution is provided whereby kitchen waste 46 is recycled into a liquid fertilizer that other residents can benefit from.

It is important to note that the screen 38 prevents any large items from passing downward and into the first zone 37. Therefore, only the effluent 32 is able to enter into the conduit 16. This is significant because it helps to ensure that the vermicomposting device 10 will not become clogged. This reduces maintenance and increases reliability.

It is also important to note that the starter mix 44 provides a significant advantage over prior art designs (not shown) which only include or suggest the use of newspaper as a bedding (i.e., as a starter habitat) for the worms 34. Newspaper has virtually no nutritional value for the worms 34 and its use can increase worm 34 mortality by depriving the worms 34 of nutrients and, thereby, stressing the worms 34. The starter mix 44 ensures that the newly added worms 34 will thrive.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A vermicomposting apparatus and system, comprising:
   (a) a container;
   (b) a conduit that includes a first end and an opposite second end, and wherein said first end is elevated with respect to said second end, and wherein said conduit is disposed in an interior of said container and proximate a bottom of said container, and wherein said second end of said conduit is attached to a member that passes through an opening provided at a bottom of said container, and wherein said conduit includes a plurality of spaced-apart fluid collection openings that extend along a longitudinal length of said conduit, wherein said fluid collection openings are disposed in two spaced-apart rows, and wherein each of said rows is disposed at a bottom of said conduit and on an opposite side of a bottom center longitudinal axis of said conduit, and wherein each of said two rows of fluid collection openings are disposed approximately 30 degrees from said bottom center longitudinal axis of said conduit and on opposite sides thereof, and wherein an effluent that is produced in said apparatus is able to flow into said conduit through said fluid collection openings that are disposed in said two spaced-apart rows, and wherein said effluent that has entered into said conduit through said fluid collection openings that are disposed in said two spaced-apart rows is able to flow downward in said conduit along said bottom center longitudinal axis of said conduit without contact or interference to the flow of said effluent by any of said fluid collection openings in said two spaced-apart rows, and wherein said conduit includes a cluster of fluid collection openings that are disposed at said second end of said conduit, and wherein said cluster is disposed at a lower elevation than any of said fluid collection openings in said two spaced-apart rows, and wherein said cluster includes a greater density and number of said fluid collection openings along a longitudinal length of said cluster than occurs along an equivalent longitudinal length of any portion of said two spaced-apart rows;
   (c) means for providing a predetermined volume at said bottom of said container that is sufficient to hold a predetermined quantity of fluid; and
   (d) a screen that is placed over said conduit and over said means for providing a predetermined volume.

2. The vermicomposting apparatus and system of claim 1 wherein said screen is flexible.

3. The vermicomposting apparatus and system of claim 1 wherein said means for providing a predetermined volume includes a quantity of gravel disposed at said bottom of said container.

4. The vermicomposting apparatus and system of claim 1 wherein said means for providing a predetermined volume includes a honeycomb type of structure that is disposed at said bottom of said container.

5. The vermicomposting apparatus and system of claim 1 wherein said conduit includes at least one vent hole that is provided at an upper portion of said conduit.

6. The vermicomposting apparatus and system of claim 1 wherein said first end of said conduit includes an end cap.

7. The vermicomposting apparatus and system of claim 1 wherein said member includes a spigot.

8. The vermicomposting apparatus and system of claim 1 including a sheet of non-porous material that is placed on top of said screen, and wherein said sheet of non-porous material is used for the harvesting of earthworm castings by urging said earthworm castings off of said sheet.

9. The vermicomposting apparatus and system of claim 1 including a starter mix that is supplied with said apparatus and which is used to provide a habitat for earthworms that are used with said apparatus, and wherein said starter mix includes nutrients for said worms to consume and thereby to better adapt to placement in said container.

10. The vermicomposting apparatus and system of claim 1 including a lid that is detachably-attachable with respect to a top of said container.

11. The vermicomposting apparatus and system of claim 1 including at least one vent attached to said container, and wherein said at least one vent includes a screen insert covering that prevents flies from entering into or exiting from said container.

12. The vermicomposting apparatus and system of claim 1 wherein said container includes at least one handle attached thereto.

13. The vermicomposting apparatus and system of claim 1 that includes a spray mister, said spray mister for supplying a quantity of water mist to said interior of said container to maintain a desired level of humidity in said container.

* * * * *